United States Patent
Suzuki et al.

(10) Patent No.: US 12,430,943 B2
(45) Date of Patent: Sep. 30, 2025

(54) CAMERA DEVICE AND CAMERA SYSTEM

(71) Applicant: JVCKENWOOD Corporation, Yokohama (JP)

(72) Inventors: Tetsuji Suzuki, Yokohama (JP); Takayuki Sugahara, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 233 days.

(21) Appl. No.: 18/461,549

(22) Filed: Sep. 6, 2023

(65) Prior Publication Data
US 2023/0419719 A1 Dec. 28, 2023

Related U.S. Application Data

(63) Continuation of application No. PCT/JP2022/008572, filed on Mar. 1, 2022.

(30) Foreign Application Priority Data

Mar. 8, 2021 (JP) ................................. 2021-036476

(51) Int. Cl.
*G06V 40/13* (2022.01)
*G06V 10/10* (2022.01)
(Continued)

(52) U.S. Cl.
CPC .......... *G06V 40/1318* (2022.01); *G06V 10/12* (2022.01); *G06V 10/17* (2022.01);
(Continued)

(58) Field of Classification Search
CPC .............. A61B 1/0005; A61B 1/00097; A61B 1/00194; A61B 1/009; A61B 2576/00; A61B 5/389; A61B 5/6826; G03B 17/00; G03B 17/24; G03B 17/56; G03B 35/02; G03B 7/00; G03B 3/014; G03B 3/015; G03B 3/0304; G06V 10/12; G06V 10/17; G06V 40/117; G06V 40/1318;
(Continued)

(56) References Cited

U.S. PATENT DOCUMENTS

2006/0038917 A1* 2/2006 Funato ................... H04N 23/50
    348/E5.025
2012/0188343 A1* 7/2012 Matsuura ............. H04N 13/221
    348/46

FOREIGN PATENT DOCUMENTS

JP          2005-159771          6/2005

OTHER PUBLICATIONS

International Search Report and Written Opinion for International Application No. PCT/JP2022/008572 mailed on Apr. 19, 2022, 8 pages.

* cited by examiner

*Primary Examiner* — Dakshesh D Parikh
(74) *Attorney, Agent, or Firm* — Amin, Turocy & Watson, LLP

(57) ABSTRACT

A camera device includes: a camera unit mounted on a finger; a biological information obtainment unit configured to obtain biological information on a palm; a camera direction detection unit configured to detect, based on the biological information obtained, a direction of the camera unit relative to a predetermined reference direction; and an output unit configured to add information on the direction of the camera unit obtained from the camera direction detection unit to imaging information captured by the camera unit, and output the resulting information.

4 Claims, 11 Drawing Sheets

(51) Int. Cl.
    *G06V 10/12* (2022.01)
    *G06V 40/10* (2022.01)
    *H04N 23/90* (2023.01)
    *H04N 23/95* (2023.01)
(52) U.S. Cl.
    CPC ........... *G06V 40/117* (2022.01); *H04N 23/90* (2023.01); *H04N 23/95* (2023.01)
(58) Field of Classification Search
    CPC ...... H04N 13/00; H04N 13/20; H04N 13/204; H04N 13/239; H04N 13/243; H04N 23/51; H04N 23/698; H04N 23/90; H04N 23/95
    See application file for complete search history.

… (1)

CAMERA DEVICE AND CAMERA SYSTEM

CROSS-REFERENCE TO RELATED APPLICATION

This application is a Continuation of International Application No. PCT/JP2022/008572, filed Mar. 1, 2022, which designates the United States, incorporated herein by reference, and which claims the benefit of priority from Japanese Patent Application No. 2021-036476, filed Mar. 8, 2021, incorporated herein by reference.

BACKGROUND

The present disclosure relates to user interfaces that control miniature cameras and particularly to a technique for controlling, by use of biological information on a palm, a camera mounted on a fingertip.

A conventionally known camera-equipped terminal includes: a stereo camera unit having a pair of left and right lenses and a pair of left and right imaging elements; a stereo finder and viewer unit including a pair of left and right eyepieces and a pair of left and right display elements; and a portable information terminal unit connected wirelessly to a public communication channel (see, for example, Japanese Unexamined Patent Application Publication No. 2005-159771). This type of camera-equipped terminal enables, completely on its own, both capturing and browsing of stereo videos.

In recent years, cameras are mounted on fingers and images captured by these cameras are displayed. A technique has been studied for this case, for example, the technique being for generating a stereo (three-dimensional) image by: mounting a camera on each of two (plural) fingers; and processing images captured by these cameras. However, this type of technique has a problem that the cameras are increased in size when gyrosensors are provided in the cameras, for example, and detection of directions (imaging directions) of the cameras mounted on the fingers is not easy.

SUMMARY

A camera device according to an embodiment includes: a camera unit mounted on a finger; a biological information obtainment unit configured to obtain biological information on a palm; a camera direction detection unit configured to detect, based on the biological information obtained, a direction of the camera unit relative to a predetermined reference direction; and an output unit configured to add information on the direction of the camera unit obtained from the camera direction detection unit to imaging information captured by the camera unit, and output the resulting information.

A camera system according to an embodiment includes: the camera device described above; and a three-dimensional image generation processing unit configured to generate, based on a plurality of captured images captured by the camera unit and directional information indicating a relative direction of the camera unit corresponding to such imaging information thus captured, three-dimensional image information representing a three-dimensional structure.

DETAILED DESCRIPTION

Embodiments will be described hereinafter in detail, on the basis of the drawings. Subject matter of the present disclosure is not limited by these embodiments. Furthermore, components in the following embodiments include those that can be easily substituted by persons skilled in the art or those that are substantially the same.

First Embodiment

Figure 1:
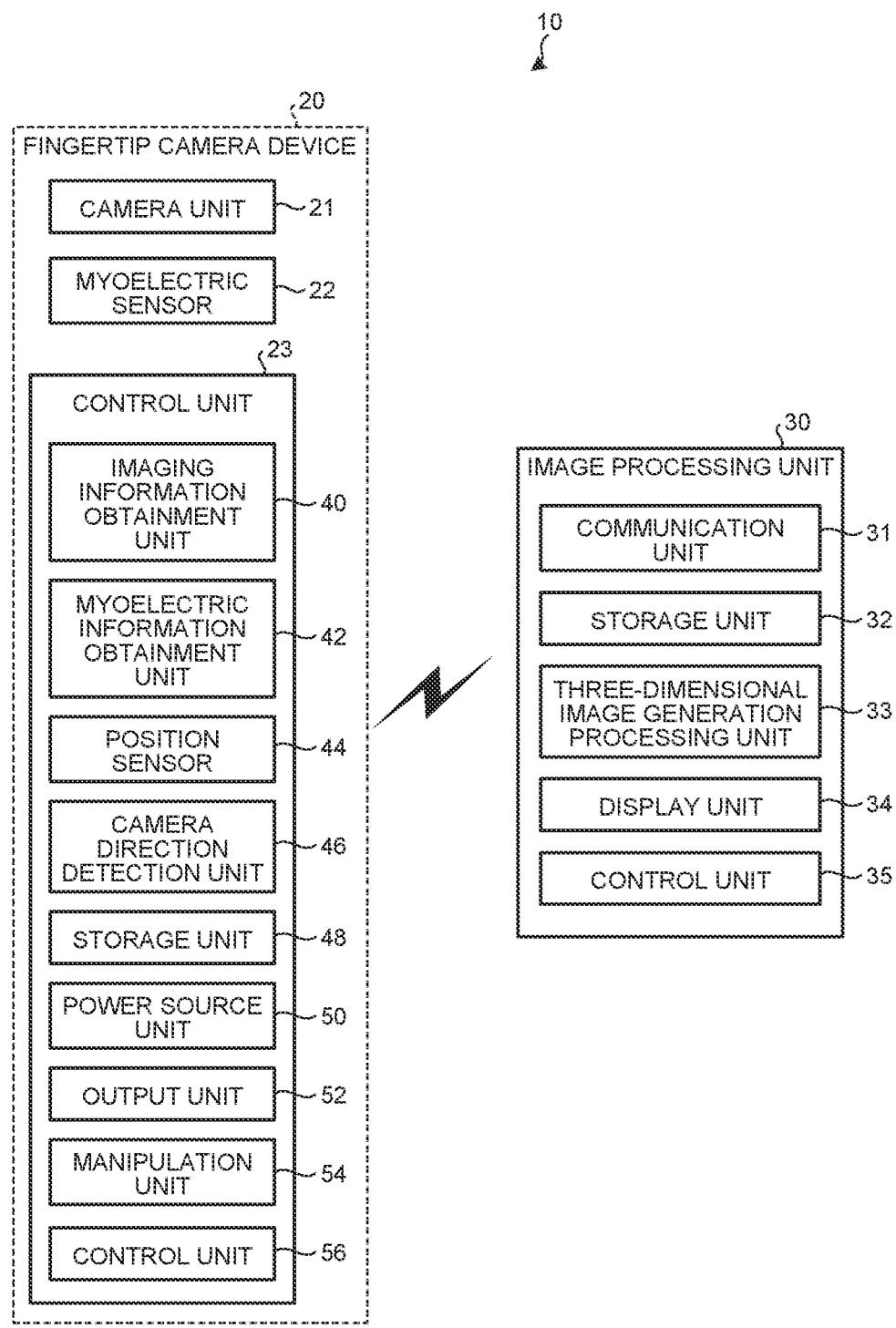
FIG. 1 is a schematic diagram illustrating an example of a fingertip camera system including a fingertip camera device according to a first embodiment.
Figure 2:
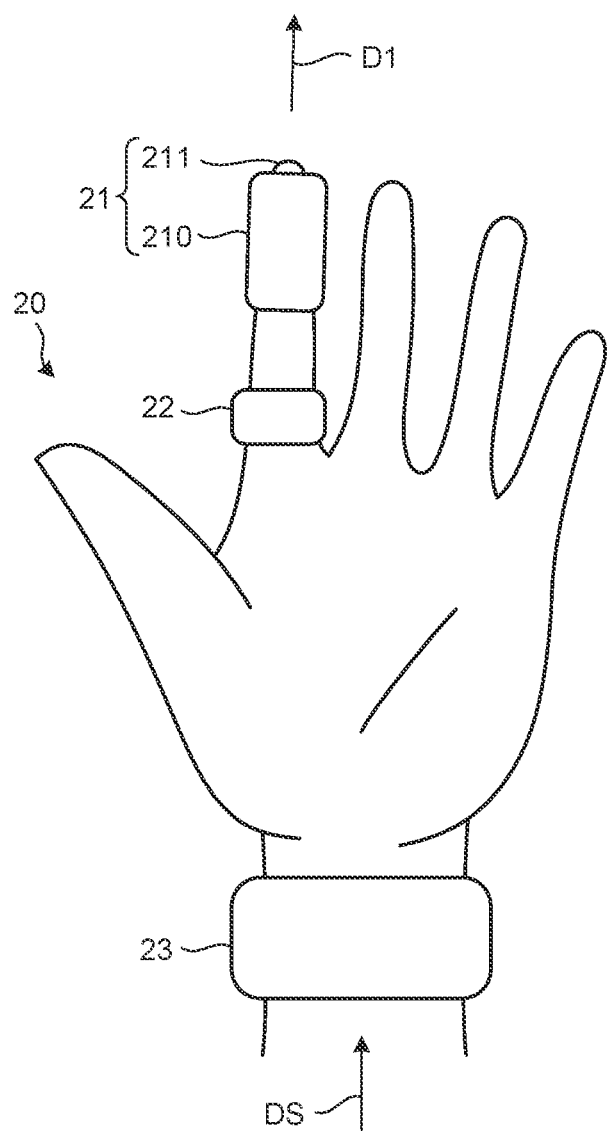
FIG. 2 is a schematic diagram illustrating an example of a state where the fingertip camera device has been mounted on a hand.

FIG. 1 is a schematic diagram illustrating an example of a fingertip camera system including a fingertip camera device according to a first embodiment. FIG. 2 is a schematic diagram illustrating an example of a state where the fingertip camera device has been mounted on a hand. In this embodiment, a fingertip camera system (camera system) 10 processes an image captured by a camera unit 21 mounted on a fingertip of a hand of a user and displays the processed image on a predetermined display unit 34.

As illustrated in FIG. 1, the fingertip camera system 10 is configured to include a fingertip camera device (camera device) 20 and an image processing unit 30. The fingertip camera device 20 and the image processing unit 30 are connected to each other via, for example, a local area network (LAN). The LAN implements relay between the fingertip camera device 20 and the image processing unit 30, and a wireless LAN, such as that of Wi-Fi (registered trademark) or a wireless communication channel, such as that of LTE or 5G, is used, for example, as the LAN.

The fingertip camera device 20 includes the camera unit, a myoelectric sensor (biological information detection unit) 22, and a control unit 23. The camera unit 21 includes, as illustrated in FIG. 2: a camera body 210 mounted on the fingertip of the hand of the user (for example, the fingertip of the index finger (second finger)); and a lens 211 provided on this camera body 210. The camera body 210 is mounted on the fingertip, like a fingerstall, by being formed in a cylindrical shape and the fingertip being inserted from an opening of the camera body 210, the cylindrical shape having a bottom. Furthermore, the camera body 210 has an image capturing unit (not illustrated in the drawings) that captures an image of surrounds of the image capturing unit via the lens 211, the image capturing unit being a built-in unit. The image captured by the imaging capturing unit is, for example, a moving image, but may also be a still image. Imaging information that has been captured is transmitted to the control unit 23 at a predetermined frequency. The lens 211 has a function of condensing light and is provided at a distal end portion (bottom portion) of the camera body 210. That is, in the example of FIG. 2, an optical axis (imaging direction) of the camera unit 21 extends in a direction of the fingertip of the finger, on which the camera unit 21 has been mounted.

The myoelectric sensor 22 is formed in a ring shape and mounted on a base portion of the finger, on which the camera unit 21 has been mounted. The myoelectric sensor 22 has a plurality of surface electrodes arranged on an inner peripheral surface of a ring-shaped body of the myoelectric sensor 22 and these surface electrodes detect myoelectric information (biological information) generated correspondingly to movement of muscles in the finger of the user. This myoelectric information is biological electric signals generated by contraction of muscles (muscle fiber) upon movement of the finger. Furthermore, the inner peripheral surface is a side that comes into contact with an outer peripheral surface of the finger of the user. The myoelectric sensor 22 detects myoelectric information generated by stretching of left and right tendons of the finger and stretching of muscles (for example, the transverse head of the adductor hallucis), for example, in a case where the finger is bent or the finger is moved horizontally to the palm so that a distance between the finger and a finger adjacent thereto is changed. The myoelectric sensor 22 is configured to be capable of detecting movement of plural muscles and tendons by this detection of the myoelectric information. The myoelectric information detected is transmitted to the control unit 23 as needed at a predetermined frequency. In this embodiment, the myoelectric sensor 22 is configured to be mounted on the base portion of the finger, on which the camera unit 21 has been mounted, but the myoelectric sensor 22 may be mounted on the base portion of the finger or on the wrist, depending on the position of the muscles corresponding to the myoelectric information to be detected. In a case where the myoelectric sensor is mounted on the wrist, the myoelectric sensor may be provided in the control unit 23.

The control unit 23 is connected to each of the camera unit 21 and the myoelectric sensor 22 and controls operation of the camera unit 21 and the myoelectric sensor 22. The control unit 23 is mounted on the wrist of the user by being wound around the wrist, for example, as illustrated in FIG. 2. In this embodiment, the control unit 23 is connected to the camera unit 21 and myoelectric sensor 22 by wire, supplies electric power to the camera unit 21 and myoelectric sensor 22, and obtains various types of information from the camera unit 21 and myoelectric sensor 22. In this embodiment, the connection is wired but without being limited to this example, the connection may be wireless. In this case, each of the camera unit 21 and the myoelectric sensor 22 preferably includes a power source (battery) for driving itself. The control unit 23 includes, as illustrated in FIG. 1, an imaging information obtainment unit 40, a myoelectric information obtainment unit (biological information obtainment unit) 42, a position sensor (arm direction detection unit) 44, a camera direction detection unit 46, a storage unit 48, a power source unit 50, an output unit 52, a manipulation unit 54, and a control unit 56.

The imaging information obtainment unit 40 is an interface that obtains imaging information transmitted from the camera unit 21. The myoelectric information obtainment unit 42 obtains myoelectric information transmitted from the myoelectric sensor 22. The obtained imaging information and myoelectric information are stored, for example, into the storage unit 48, in association with the camera unit 21.

The position sensor 44 is a sensor that detects a position and a direction of the control unit 23 and is configured to include, for example, a gyrosensor, a triaxial acceleration sensor, or a geomagnetic sensor. This position sensor 44 enables detection of: a position of the wrist (arm) of the user, on which the control unit 23 has been mounted; and a direction in which the arm of the user extends. The following description is on a specific example in which the direction in which the arm extends is calculated. For example, two or more position sensors 44 are installed in the control unit 23. The two or more position sensors 44 are installed in the control unit 23 so that the two or more position sensors 44 are positioned on a line of the direction in which the wrist extends upon attachment of the control unit 23 to the wrist by the user. Joining the positions of the position sensors 44 enables detection of the extending direction. Furthermore, the number of the position sensors 44 may be one, and the direction in which the arm extends may be calculated from a change in position detected by the position sensor 44.

The camera direction detection unit 46 detects, based on the myoelectric information obtained, a direction (imaging direction) of the camera unit 21 relative to a predetermined reference direction. In this configuration, the reference direction is the direction detected by the position sensor 44 in which the arm of the user extends, and the direction of the camera unit 21 relative to that direction in which the arm extends is detected. A direction in which the finger is bent, that is, a direction of the camera unit 21 relative to the palm, is calculated as, for example, a three-dimensional directional vector from myoelectric information. In this case, data defining a relation between myoelectric information on a muscle at the base of the finger (for example, the transverse head of the adductor hallucis, the internal oblique muscle of the thumb, the abductor pollicis brevis, or the flexor hallucis brevis) and directional information (directional vector) on movement of the finger at that time are called up from the storage unit 48, directional information (direction vector) on movement of the finger is calculated by comparison between obtained myoelectric information and these data, and the direction of the camera unit 21 relative to the palm is thereby able to be calculated. Furthermore, by use of myoelectric information measured for the muscle at the base of the finger (for example, the transverse head of the adductor hallucis, the internal oblique muscles of the thumb, the abductor pollicis brevis, or the flexor hallucis brevis) and directional information (directional vectors) on movement of the finger at that time, a trained model resulting from machine learning is generated, with these pieces of information serving as a training data set, and the direction of the camera unit 21 relative to the palm is able to be calculated by input of detected myoelectric information, into this trained model. Furthermore, the direction in which the arm extends is calculated as a three-dimensional directional vector through detection by the position sensor/sensors. Therefore, having the direction in which the arm extends as the reference direction enables detection (calculation) of the direction of the camera unit 21 relative to that reference direction.

The storage unit 48 is configured to include, for example, a RAM or a flash memory, and stores imaging information and myoelectric information that have been obtained. The storage unit 48 also stores a direction (imaging direction) of the camera unit 21 relative to the predetermined reference direction. Furthermore, the storage unit 48 stores the trained model described above. This trained model is generated by machine learning, with myoelectric information and directional information both serving as a training data set, the myoelectric information having been generated upon movement of the finger, the directional information (directional vectors) being on the movement of the finger at that time.

The power source unit 50 is a power source for driving the fingertip camera device 20. This power source unit 50 is, for example, a rechargeable battery and supplies electric power to the camera unit 21 and the myoelectric sensor 22. The output unit 52 outputs information from the control unit 23 to the image processing unit 30. In this embodiment, the output unit 52 is an interface that adds relative directional information on the camera unit 21, the relative directional information having been detected by the camera direction detection unit 46, to imaging information captured by the camera unit 21, and outputs the relative directional information that has been added to the imaging information. In this case, the directional information and the imaging information may be output correspondingly to (in association with) each other.

The manipulation unit 54 is for manipulating operation of the fingertip camera device 20. For example, the manipulation unit 54 includes a switch formed on a surface of the control unit 23 mounted on the wrist and a start manipulation and a stop manipulation for imaging operation of the camera unit 21 is implemented by manipulation of this switch. The control unit 56 controls operation of each component of the control unit 23.

The myoelectric information obtainment unit 42, the camera direction detection unit 46, and the control unit 56 each include a CPU, a ROM, and a RAM, for example.

The image processing unit 30 includes, as illustrated in FIG. 1, a communication unit 31, a storage unit 32, a three-dimensional image generation processing unit 33, the display unit 34, and a control unit 35. Specifically, the image processing unit 30 is an information processing device, such as a computer device or a smartphone. Furthermore, the three-dimensional image generation processing unit 33 and the control unit 35 of the image processing unit 30 include, for example, a CPU, a ROM, and a RAM. Specific examples of the communication unit 31, the storage unit 32, and the display unit 34 will be described later.

The communication unit 31 is an interface that receives relative directional information on the camera unit 21 and imaging information both output from the control unit 23 of the fingertip camera device 20. The storage unit 32 stores: various types of information that have been received; and a control program. A semiconductor memory element, such as a flash memory, may be used, for example, as the storage unit 32, but the storage unit 32 may be a storage device, such as an HDD.

The three-dimensional image generation processing unit 33 generates three-dimensional image information representing a three-dimensional structure, from a plurality of captured images. The three-dimensional image generation processing unit 33 may generate the three-dimensional image information by using a so-called photogrammetry technique. The three-dimensional image generation processing unit 33 extracts a target to be captured, as features points, from a plurality of pieces of imaging information captured by the fingertip camera device 20, and generates the three-dimensional image information by performing association of the feature points extracted from the a plurality of pieces of imaging information, on the basis of directional information on a plurality of cameras corresponding to these pieces of imaging information. The three-dimensional image information generated is stored into the storage unit 32. Furthermore, a three-dimensional image may be, for example, a three-dimensional model formed of a three-dimensional point cloud in a predetermined coordinate system.

The display unit 34 is, for example, a monitor unit including a liquid crystal display (LCD) and displays three-dimensional image information that has been generated. In this embodiment, the display unit 34 is configured to be integrally provided with the image processing unit 30 but the display unit 34 may be separately bodied as, for example, an eyeglass display, such as a head-mounted display. The control unit 35 controls the overall operation of the image processing unit 30.

Figure 3:
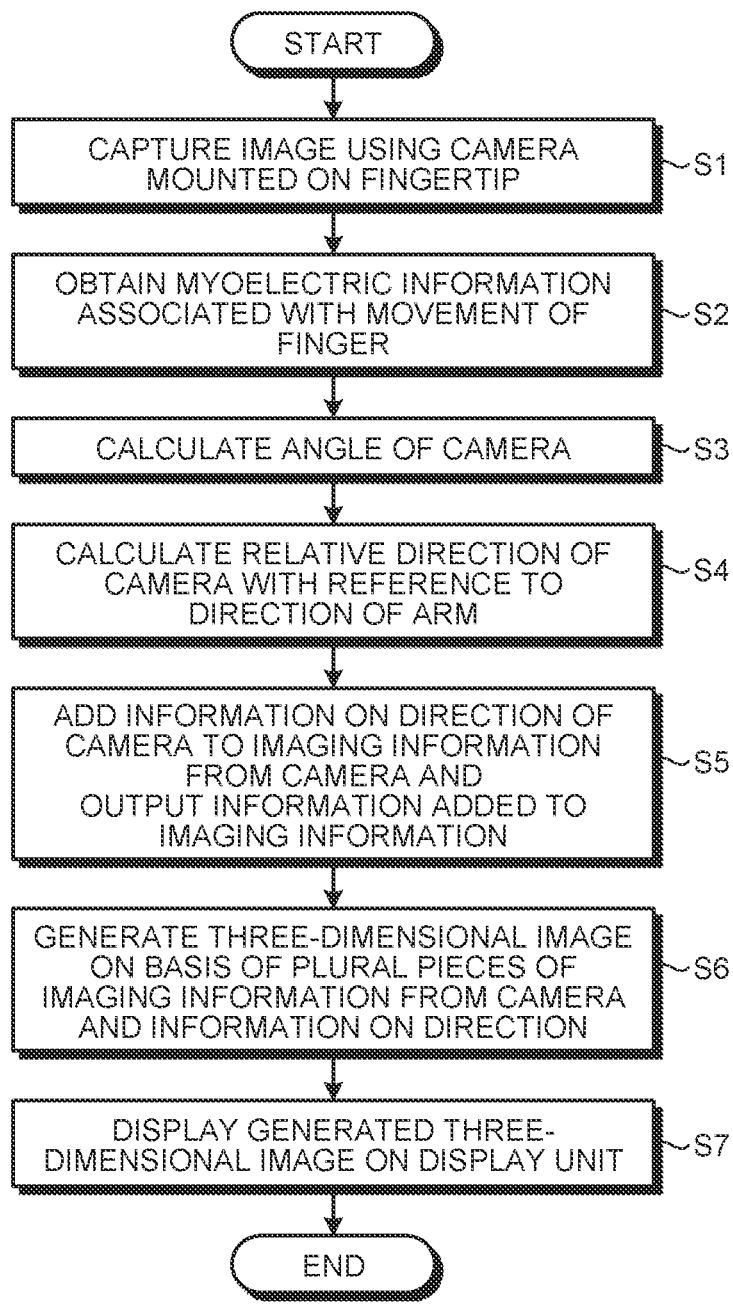
FIG. 3 is a flowchart illustrating a procedure of operation by the fingertip camera system.

Operation of the fingertip camera system will be described next. FIG. 3 is a flowchart illustrating a procedure of the operation by the fingertip camera system. Before the operation, the fingertip camera device 20 described above is mounted on a hand of a user. In this embodiment, as illustrated in FIG. 2, the camera unit 21 is mounted on the fingertip of the index finger and the myoelectric sensor 22 is mounted on the base portion of the index finger. Furthermore, the control unit 23 is mounted on the wrist. A state where the index finger has been stretched out straight along the arm is a basic state, in this case.

Firstly, the manipulation unit 54 of the control unit 23 is manipulated and an image is thereby captured by the camera unit 21 mounted on the fingertip (Step S1). In this case, imaging information captured is transmitted from the camera unit 21 to the control unit 23 and the imaging information obtainment unit 40 obtains the imaging information. Subsequently, the myoelectric sensor 22 detects myoelectric information associated with movement of the finger during imaging, transmits the myoelectric information to the control unit 23, and the myoelectric information obtainment unit 42 obtains the myoelectric information (Step S2). The imaging information and the myoelectric information are stored into the storage unit 48 correspondingly to each other.

Subsequently, the camera direction detection unit 46 calculates a bending direction of the finger, that is, an angle (direction) of the camera unit 21 to the palm, on the basis of the myoelectric information first (Step S3). In this case, a trained model is generated beforehand, the trained model resulting from machine learning with a training data set that is myoelectric information measured for a muscle at the bases of the finger (for example, the transverse head of the adductor hallucis, the internal oblique muscle of the thumb, the abductor pollicis brevis, or the flexor hallucis brevis) and directional information (directional vectors) on movement of the finger at that time, and the camera direction detection unit 46 calculates an angle (direction) of the camera unit 21 to the palm by inputting the detected myoelectric information into this trained model. Information on this calculated angle of the camera unit 21 is, for example, a three-dimensional directional vector.

Subsequently, the camera direction detection unit 46 detects a relative direction (imaging direction) of the camera unit 21, with a direction of the arm serving as a reference direction (Step S4). The camera direction detection unit 46 obtains a direction DS detected by the position sensor 44, the direction DS being a direction in which the arm of the user extends. This direction DS in which the arm extends is calculated as a three-dimensional directional vector. By having this direction in which the arm extends, as the reference direction, the camera direction detection unit 46 detects (calculates) a direction D1 of the camera unit 21 relative to that reference direction.

Subsequently, the output unit 52 adds the relative directional information on the camera unit 21 and obtained from the camera direction detection unit 46, to the imaging information captured by the camera unit 21, and outputs the relative directional information that has been added to the imaging information, to the image processing unit 30 (Step S5). In this case, a method in which the directional information is multiplexed with the imaging information (for example, data of an MPEG movie compression format) may be adopted.

Subsequently, the three-dimensional image generation processing unit 33 of the image processing unit 30 generates three-dimensional image information representing a three-dimensional structure, on the basis of a plurality of captured images captured by the camera unit 21 and directional information indicating a relative direction of the camera unit, the relative direction corresponding to these pieces of imaging information (Step S6). In this case, the three-dimensional image generation processing unit 33 may generate the three-dimensional image information by using a so-called photogrammetry technique. That is, the three-dimensional image generation processing unit 33 extracts a target to be captured, as features points, from a plurality of pieces of imaging information captured at predetermined time intervals by the fingertip camera device 20, and generates the three-dimensional image information by performing association of the feature points extracted from the a plurality of pieces of imaging information, on the basis of directional information on a plurality of cameras corresponding to these pieces of imaging information.

Subsequently, the control unit 35 of the image processing unit 30 displays the three-dimensional image information generated, on the display unit 34 (Step S7) and ends processing.

In this embodiment, because the camera unit 21 is mounted on a fingertip, just pointing at a distant view or a nearby object enables imaging easily, and for example, an enlarged video (image) is able to be captured by the camera unit 21 approaching, like a magnifying glass, a small target. Furthermore, the myoelectric sensor 22 enables obtainment of information at the same time, the information being related to a direction of the finger on which the camera unit 21 has been mounted, and an imaging direction of the camera unit 21 mounted on the fingertip is thus able to be detected easily.

Second Embodiment

Figure 4:
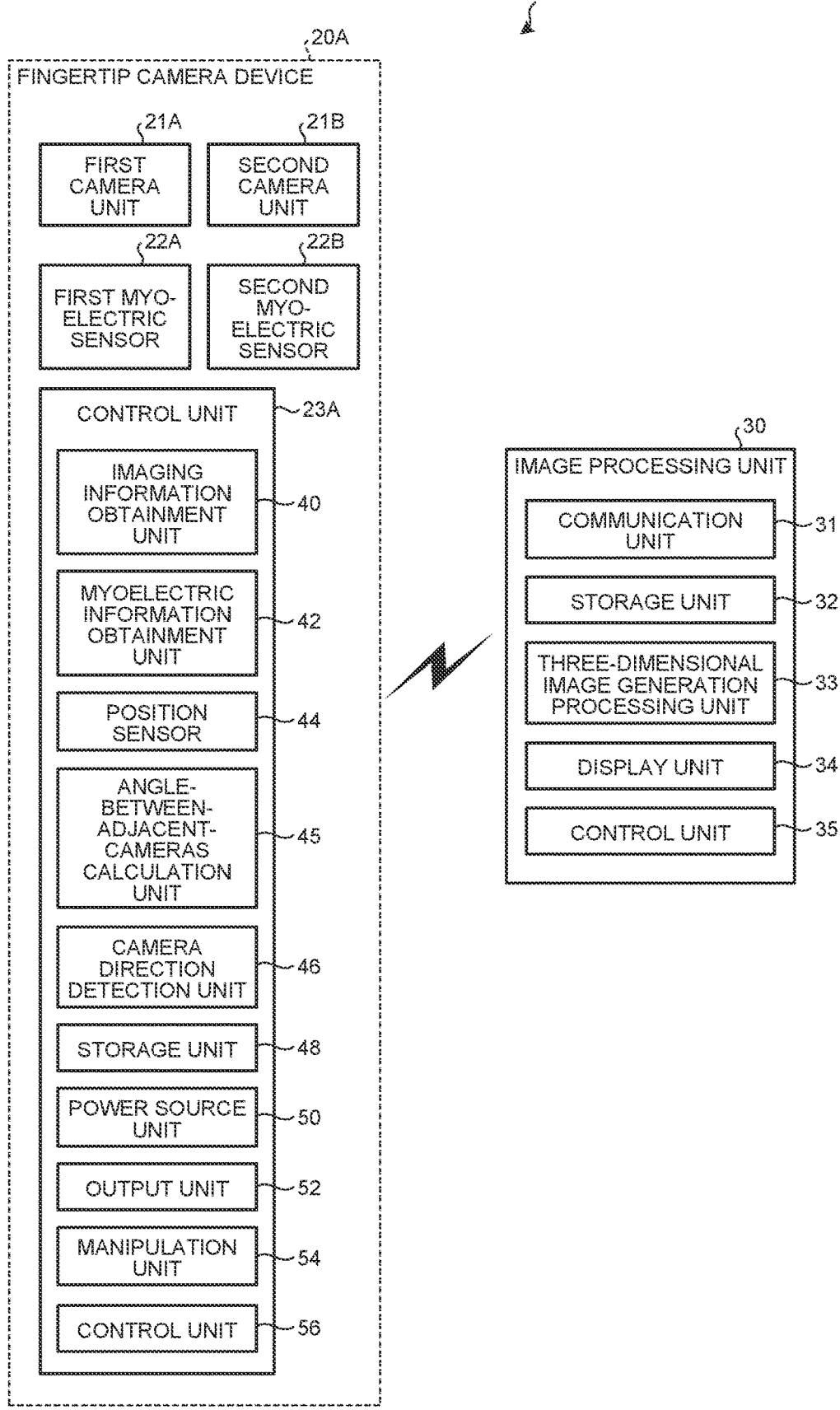
FIG. 4 is a schematic diagram illustrating an example of a fingertip camera system including a fingertip camera device according to a second embodiment.
Figure 5:
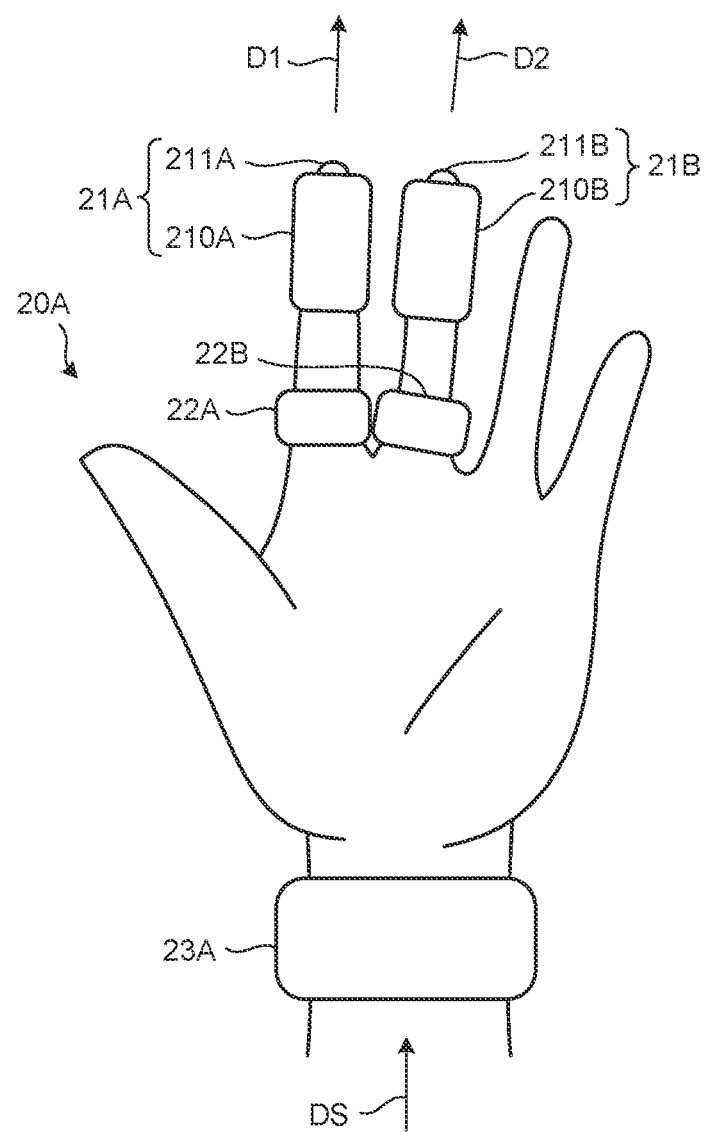
FIG. 5 is a schematic diagram illustrating an example of a state where the fingertip camera device has been mounted on a hand.

FIG. 4 is a schematic diagram illustrating an example of a fingertip camera system including a fingertip camera device according to a second embodiment. FIG. 5 is a schematic diagram illustrating an example of a state where the fingertip camera device has been mounted on a hand. In the first embodiment, the fingertip camera device 20 is configured to include one camera unit 21 and one myoelectric sensor 22, but the fingertip camera device in this second embodiment is different from the fingertip camera device 20 in that the fingertip camera device includes a plurality of the camera units 21 and a plurality of the myoelectric sensors 22. The same reference signs will be assigned to components that are the same as those of the above-described embodiment and description thereof will be omitted.

As illustrated in FIG. 4, a fingertip camera system 10A is configured to include a fingertip camera device 20A and an image processing unit 30. The fingertip camera device 20A includes two camera units 21A and 21B, two myoelectric sensors (biological information detection units) 22A and 22B, and a control unit 23A. One of the camera units, the camera unit 21A, is mounted on a fingertip (for example, the fingertip of the index finger (second finger)) of a hand of a user and the other one of the camera units, the camera unit 21B, is mounted on the next fingertip (for example, the fingertip of the middle finger (third finger)). In this embodiment, a pair of the two camera units 21A and 21B functions as a stereo camera in cooperation with each other. Specifically, a stereo image is able to be captured from images respectively captured by the camera units 21A and 21B by utilization of a disparity between the camera units 21A and 21B mounted on the fingertips next to each other. The camera units 21A and 21B and myoelectric sensors 22A and 22B are configured similarly to those in the above-described embodiment.

The control unit 23A is different from the control unit 23 of the above-described embodiment in that the control unit 23A includes an angle-between-adjacent-cameras calculation unit 45. On the basis of myoelectric information on the fingertips respectively detected by the two myoelectric sensors 22A and 22B, the angle-between-adjacent-cameras calculation unit 45 calculates an angle between the camera units 21A and 21B adjacent to each other (an angle mainly horizontal to the palm when the fingers are spread apart or brought together). As described above, directions (angles) of the camera units 21A and 21B relative to the palm are able to be calculated by input of the detected myoelectric information into a predetermined trained model. Therefore, the angle between the camera units 21A and 21B adjacent to each other is able to be calculated from the directions (angles) of these camera units 21A and 21B. This configuration enables calculation of a disparity between the camera units 21A and 21B that function as a stereo camera and thus a stereo image is able to be captured accurately.

Figure 6:
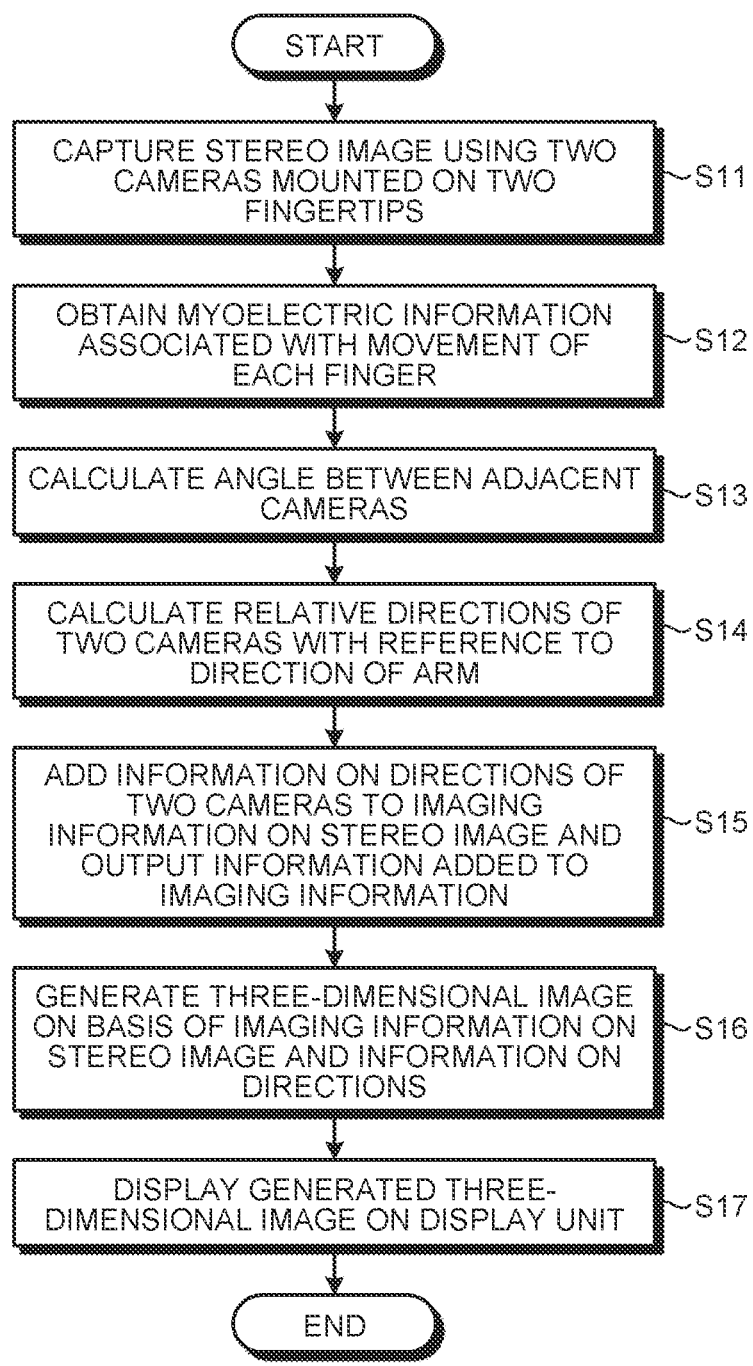
FIG. 6 is a flowchart illustrating a procedure of operation by the fingertip camera system.

Operation of the fingertip camera system 10A will be described next. FIG. 6 is a flowchart illustrating a procedure of the operation by the fingertip camera system. In this embodiment, as illustrated in FIG. 5, the camera unit 21A is mounted on the fingertip of the index finger and the myoelectric sensor 22A is mounted on the base portion of the index finger. Furthermore, the camera unit 21B is mounted on the fingertip of the middle finger and the myoelectric sensor 22B is mounted on the base portion of the middle finger. Furthermore, the control unit 23A is mounted on the wrist.

Firstly, a manipulation unit 54 of the control unit 23A is manipulated and a stereo image is thereby captured by the two camera units 21A and 21B mounted on the two fingertips (Step S11). In this case, imaging information captured is transmitted from the camera units 21A and 21B to the control unit 23A and an imaging information obtainment unit 40 obtains the imaging information. Subsequently, the myoelectric sensors 22A and 22B detect myoelectric information associated with movement of the fingertips respectively during imaging, transmits the myoelectric information to the control unit 23A, and the myoelectric information obtainment unit 42 obtains the myoelectric information on the fingertips (Step S12). The imaging information and the myoelectric information are stored into a storage unit 48 correspondingly to each other.

Subsequently, the angle-between-adjacent-cameras calculation unit 45 calculates an angle between the camera units 21A and 21B adjacent to each other, on the basis of the myoelectric information on the fingertips, the myoelectric information having been detected by the two myoelectric sensors 22A and 22B (Step S13). Subsequently, a camera direction detection unit 46 detects a relative direction (imaging direction) of each of the camera units 21A and 21B, with a direction of the arm serving as a reference direction (Step S14). The camera direction detection unit 46 obtains a direction DS detected by a position sensor 44, the direction DS being a direction in which the arm of the user extends. This direction DS in which the arm extends is calculated as a three-dimensional directional vector. By having this direction in which the arm extends, as the reference direction, the camera direction detection unit 46 detects (calculates) a direction D1 of the camera unit 21A relative to the reference direction, and a direction D2 of the camera unit 21B relative to the reference direction.

Subsequently, the output unit 52 adds the relative directional information on the camera units 21A and 21B, the relative directional information having been obtained from the camera direction detection unit 46, to imaging information on a stereo image captured by the camera units 21A and 21B, and outputs the relative directional information that has been added to the imaging information, to the image processing unit 30 (Step S15). In this case, a method in which the directional information is multiplexed with the imaging information (for example, data of an MPEG movie compression format) may be adopted.

Subsequently, a three-dimensional image generation processing unit 33 of the image processing unit 30 generates three-dimensional image information representing a three-dimensional structure, on the basis of captured images for a plurality of stereo images captured by the camera units 21A and 21B and directional information indicating relative directions of the camera units 21A and 21B, the relative directions corresponding to these pieces of imaging information (Step S16). In this case, the three-dimensional image generation processing unit 33 may generate the three-dimensional image information by using a so-called photogrammetry technique. That is, the three-dimensional image generation processing unit 33 extracts a target to be captured, as features points, from imaging information on the a plurality of stereo images captured at predetermined time intervals by the fingertip camera device 20A, and generates the three-dimensional image information by performing association of the feature points extracted from the a plurality of pieces of imaging information, on the basis of the directional information on the plurality of cameras, the directional information corresponding to these pieces of imaging information.

Subsequently, a control unit 35 of the image processing unit 30 displays the three-dimensional image information generated, on a display unit 34 (Step S17) and ends processing.

In this embodiment, because the camera units 21 are mounted on fingertips, just pointing at a distant view or a nearby object enables imaging easily, and for example, an enlarged video (image) is able to be captured by the camera units 21 approaching, like a magnifying glass, a small target. Furthermore, the myoelectric sensors 22 enable obtainment of information at the same time, the information being related to directions of the fingers on which the camera units 21 have been mounted, and imaging directions of the camera units 21 mounted on the fingertips are thus able to be detected easily. Furthermore, because two camera units 21A and 21B are included in this embodiment, a stereo image (disparity image) is able to be obtained and a three-dimensional image using a disparity is able to be generated. Furthermore, using imaging information from viewpoints of the two camera units 21A and 21B enables reconstruction of three-dimensional spatial information.

Third Embodiment

Figure 7:
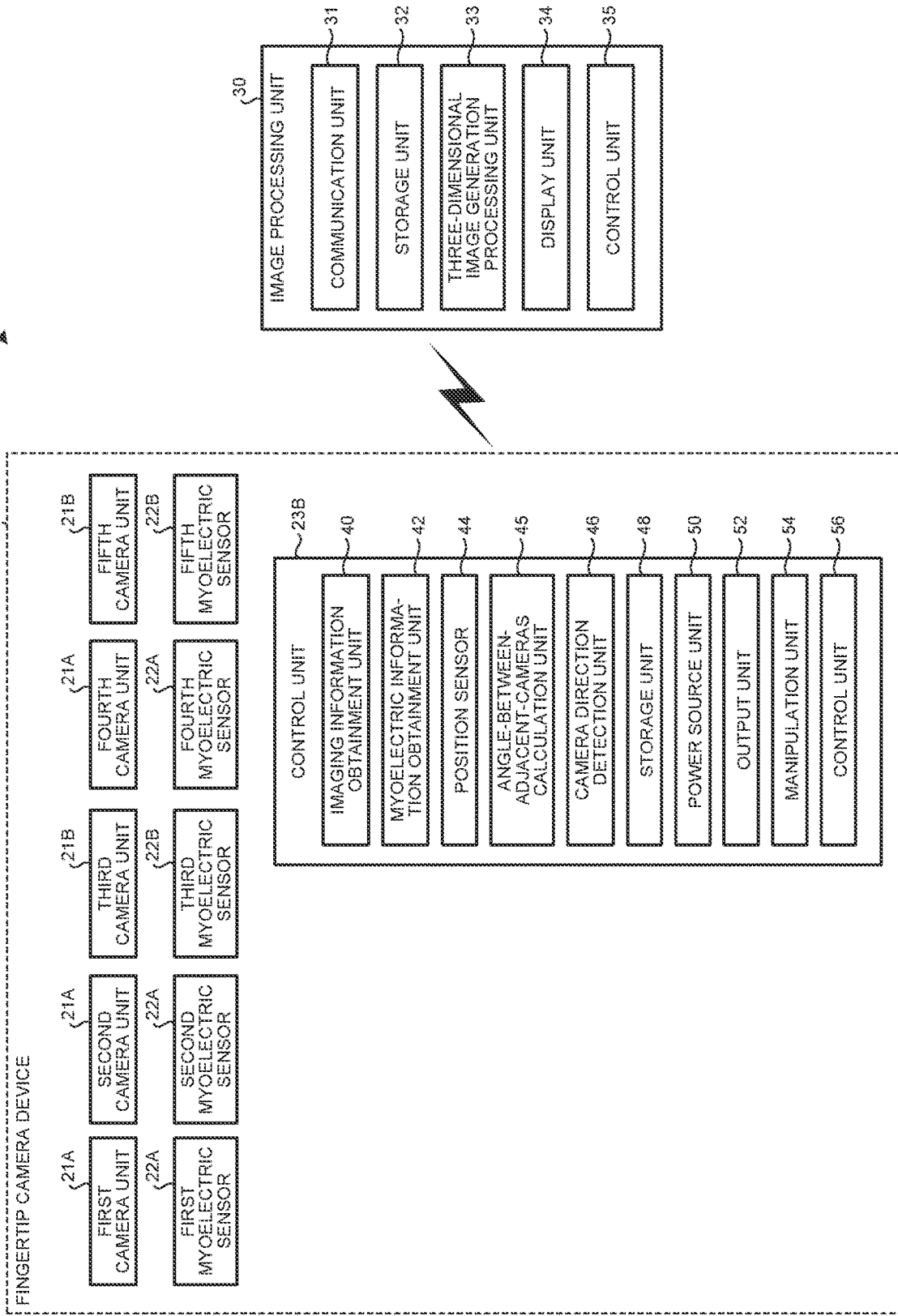
FIG. 7 is a schematic diagram illustrating an example of a fingertip camera system including a fingertip camera device according to a third embodiment.
Figure 8:
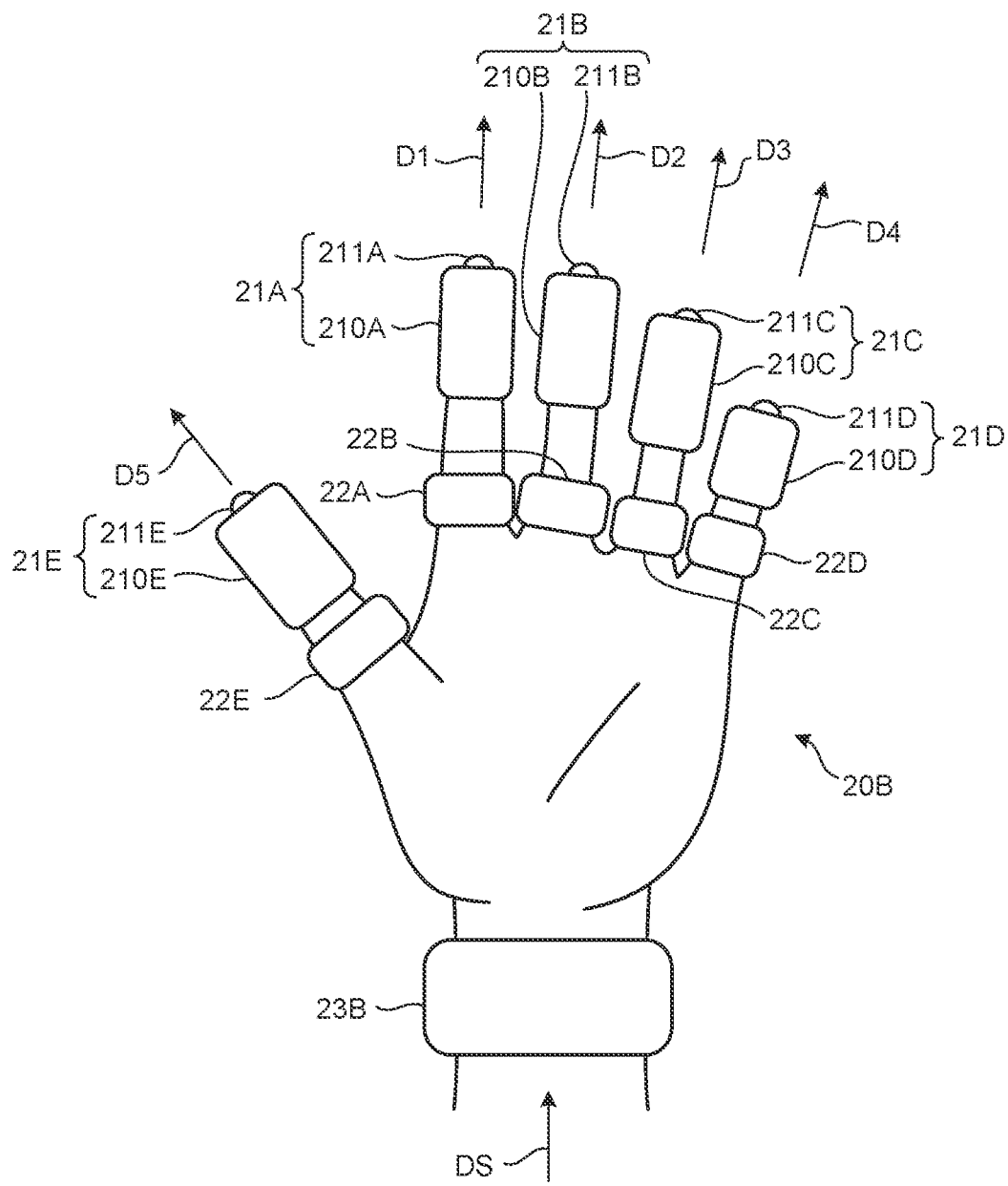
FIG. 8 is a schematic diagram illustrating an example of a state where the fingertip camera device has been mounted on a hand.

FIG. 7 is a schematic diagram illustrating an example of a fingertip camera system including a fingertip camera device according to a third embodiment. FIG. 8 is a schematic diagram illustrating an example of a state where the fingertip camera device has been mounted on a hand. In the second embodiment, the fingertip camera device 20A is configured to include the two camera units 21A and 21B and the two myoelectric sensors 22A and 22B, but this third embodiment is different from the second embodiment in that five camera units 21A to 21E and five myoelectric sensors 22A to 22E are included. The same reference signs will be assigned to components that are the same as those of the above-described embodiments and description thereof will be omitted.

As illustrated in FIG. 7, a fingertip camera system 10B is configured to include a fingertip camera device 20B and an image processing unit 30. The fingertip camera device 20B includes the five camera units 21A to 21E, the five myoelectric sensors (biological information detection units) 22A to 22E, and a control unit 23B. The first camera unit 21A is mounted on a fingertip of a hand of a user (for example, the fingertip of the index finger (second finger)) and the second camera unit 21B is mounted on the next fingertip (for example, the fingertip of the middle finger (third finger)). Furthermore, the third camera unit 21C is mounted on the next fingertip (for example, the fingertip of the ring finger (fourth finger)) and the fourth camera unit 21D is mounted on the next fingertip (for example, the fingertip of the little finger (fifth finger)). Furthermore, the fifth camera unit 21E is mounted on another fingertip (for example, the finger tip of the thumb (first finger)). The reference signs of the camera units and the fingers on which the camera units are mounted have been assigned for convenience of description and may be modified as appropriate. Similarly, the myoelectric sensors 22A to 22E are mounted respectively on the base portions of these fingers.

The control unit 23B is different from the control unit 23 of the above-described embodiment in that the control unit 23B includes an angle-between-adjacent-cameras calculation unit 45. On the basis of myoelectric information on the fingers, the myoelectric information having been detected by the five myoelectric sensors 22A to 22E, the angle-between-adjacent-cameras calculation unit 45 calculates an angle between two adjacent ones of the camera units (an angle mainly horizontal to the palm when the fingers are spread apart or brought together). As described above, directions (angles) of the camera units 21A and 21E relative to the palm are able to be calculated by input of detected myoelectric information into a predetermined trained model. Therefore, the angle between two adjacent ones of the camera units is able to be calculated from the directions (angles) of these camera units 21A to 21E.

Figure 9:
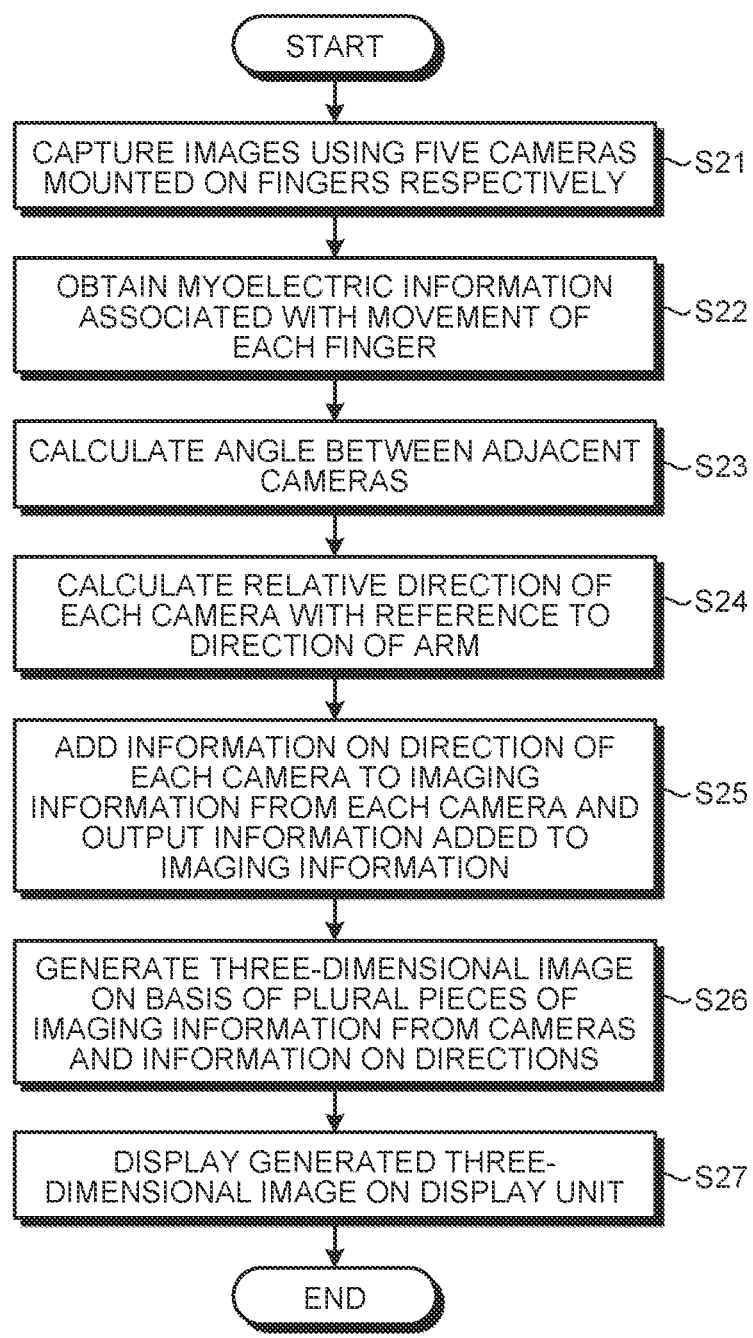
FIG. 9 is a flowchart illustrating a procedure of operation by the fingertip camera system.

Operation of the fingertip camera system 10B will be described next. FIG. 9 is a flowchart illustrating a procedure of the operation by the fingertip camera system. In this embodiment, as illustrated in FIG. 8, the camera unit 21A is mounted on the fingertip of the index finger and the myoelectric sensor 22A is mounted on the base portion of the index finger. Furthermore, the camera unit 21B is mounted on the fingertip of the middle finger and the myoelectric sensor 22B is mounted on the base portion of the middle finger. Furthermore, the camera unit 21C is mounted on the fingertip of the ring finger and the myoelectric sensor 22C is mounted on the base portion of the ring finger. Furthermore, the camera unit 21D is mounted on the fingertip of the little finger and the myoelectric sensor 22D is mounted on the base portion of the little finger. Furthermore, the camera unit 21E is mounted on the fingertip of the thumb and the myoelectric sensor 22E is mounted on the base portion of the thumb. Furthermore, the control unit 23B is mounted on the wrist.

Firstly, a manipulation unit 54 of the control unit 23B is manipulated and images are thereby captured respectively by the five camera units 21A to 21E mounted on the five fingertips (Step S21). In this case, pieces of imaging information captured are transmitted respectively from the camera units 21A to 21E and the imaging information obtainment unit 40 obtains the pieces of imaging information transmitted. Subsequently, the myoelectric sensors 22A to 22E respectively detect myoelectric information associated with movement of the fingers during imaging, transmit the detected myoelectric information, to the control unit 23B, and the myoelectric information obtainment unit 42 obtains the transmitted myoelectric information on the fingers (Step S22). The imaging information and myoelectric information are stored into a storage unit 48, correspondingly to each other.

Subsequently, the angle-between-adjacent-cameras calculation unit 45 calculates an angle between two adjacent ones of the camera units, on the basis of the myoelectric information on the fingers, the myoelectric information having been detected by the five myoelectric sensors 22A to 22E (Step S23). Subsequently, a camera direction detection unit 46 detects a relative direction (imaging direction) of each of the camera units 21A to 21E, with a direction of the arm serving as a reference direction (Step S24). The camera direction detection unit 46 obtains a direction DS detected by a position sensor 44, the direction DS being a direction in which the arm of the user extends. This direction DS in which the arm extends is calculated as a three-dimensional directional vector. By having this direction in which the arm extends as the reference direction, the camera direction detection unit 46 detects (calculates) a direction D1 of the camera unit 21A, a direction D2 of the camera unit 21B, a direction D3 of the camera unit 21C, a direction D4 of the camera unit 21D, and a direction D5 of the camera unit 21E, the directions D1 to D5 being relative to the reference direction.

Subsequently, an output unit 52 respectively adds the relative directional information on the camera units 21A to 21E obtained from the camera direction detection unit 46 to the pieces of imaging information respectively captured by the camera units 21A to 21E and outputs the relative directional information that has been added to the pieces of imaging information, to the image processing unit 30 (Step S25). In this case, a method in which the directional information is multiplexed with the imaging information (for example, data of an MPEG movie compression format) may be adopted.

Subsequently, a three-dimensional image generation processing unit 33 of the image processing unit 30 generates three-dimensional image information representing a three-dimensional structure, on the basis of a plurality of captured images respectively captured by the camera units 21A to 21E and directional information indicating relative directions of the camera units 21A to 21E, the relative directions corresponding to these pieces of imaging information (Step S26). In this case, the three-dimensional image generation processing unit 33 may generate the three-dimensional image information by using a so-called photogrammetry technique. That is, the three-dimensional image generation processing unit 33 extracts a target to be captured, as features points, from a plurality of pieces of imaging information captured by the camera units 21A to 21E of the fingertip camera device 20B, and generates the three-dimensional image information by performing association of the feature points extracted from the plurality of pieces of imaging information, on the basis of directional information on a plurality of cameras, the directional information corresponding to these pieces of imaging information.

Subsequently, a control unit 35 of the image processing unit 30 displays the three-dimensional image information generated, on a display unit 34 (Step S27) and ends processing.

In this embodiment, because the camera units 21 are mounted on fingertips, just pointing at a distant view or a nearby object enables imaging easily, and for example, an enlarged video (image) is able to be captured by the camera units 21 approaching, like a magnifying glass, a small target. Furthermore, the myoelectric sensors 22 enable obtainment of information at the same time, the information being related to directions of the fingers on which the camera units 21 are mounted, and imaging directions of the camera units 21 mounted on the fingertips are thus able to be detected easily. Furthermore, because the five camera units 21A to 21E are included in this embodiment, imaging of space ahead of each finger around the palm, like a palm holding a ball, is enabled, for example, in a state where the five camera units have disparities between each other. Therefore, on the basis of the five pieces of imaging information obtained and directional information on the camera units, the directional information being relative to the arm, a space defined by a depth and vertical and horizontal disparities is able to be calculated from the five pieces of image information and a three-dimensional image is thereby able to be generated.

Figure 10:
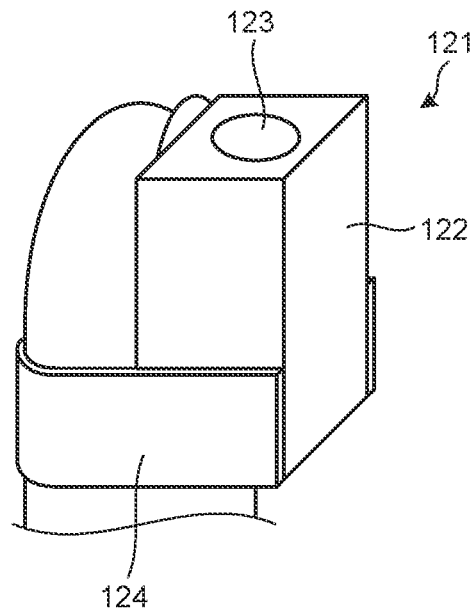
FIG. 10 is a diagram illustrating a schematic configuration of a camera unit according to a modified example.
Figure 11:
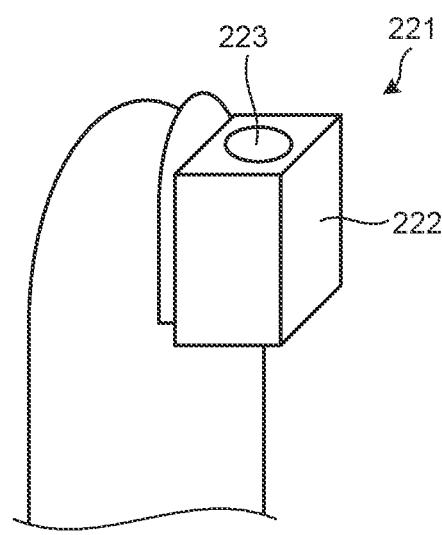
FIG. 11 is a diagram illustrating a schematic configuration of a camera unit according to a modified example.
Figure 12:
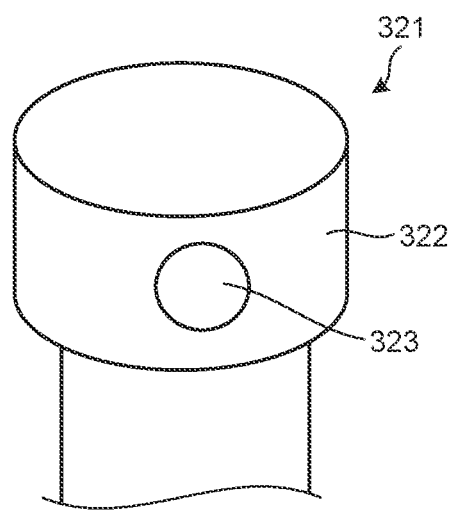
FIG. 12 is a diagram illustrating a schematic configuration of a camera unit according to a modified example.

Modified examples will be described next. FIG. 10 to FIG. 12 are diagrams each illustrating a schematic configuration of a camera unit according to a modified example. In the example of FIG. 10, a camera unit 121 includes a camera body 122 arranged on a fingertip, a lens provided on this camera body 122, and a ring 124 for mounting the camera body 122 on the fingertip. In this configuration, in contrast with the fingerstall type described above with respect to the embodiments, the pad of the finger is free and thus detailed work using the fingertip and fingerprint authentication are not hindered.

Furthermore, in the example of FIG. 11, a camera unit 221 includes a camera body 222 arranged on a fingertip and a lens 223 provided on this camera body 222. The camera body 222 has been attached to a fingernail by means of an adhesive or a suction cup. Because a ring is not used in this configuration, the pad of the finger is even more free and thus detailed work using the fingertip and fingerprint authentication are able to be performed easily.

Furthermore, in the example of FIG. 12, a camera unit 321 is of the fingerstall type, similarly to the above-described embodiments, and includes: a camera body 322 into which a fingertip is inserted, the camera body 322 having a cylindrical shape with a bottom; and a lens 323 provided on an outer peripheral surface of this camera body 322. This lens 323 is arranged on the pad of the finger, for example. When the camera unit 321 configured as described above is mounted on each of the five fingers and each of the fingers is bent, each of the camera units 321 is arranged on a circular arc formed by the fingertip, and thus imaging is enabled in a state where a target to be captured is surrounded over 360 degrees and a three-dimensional image is able to be formed easily.

In the above-described embodiments, the fingertip camera device 20 enables easy detection of a direction of the camera unit 21 mounted on a fingertip because the fingertip camera device 20 includes: the camera unit 21 mounted on the fingertip of a hand; the myoelectric information obtainment unit 42 that obtains myoelectric information on the palm; the camera direction detection unit 46 that detects, based on the myoelectric information obtained, a direction of the camera unit 21 relative to a predetermined reference direction; and the output unit 52 that adds the directional information on the camera unit 21, the directional information having been obtained from the camera direction detection unit 46, to imaging information captured by the camera unit 21, and outputs the directional information that has been added to the imaging information.

Furthermore, the myoelectric information obtainment unit 42 obtains the myoelectric information associated with movement of the finger on which the camera unit 21 has been mounted, and the direction of the camera unit 21 is thus able to be detected easily, the direction being associated with the movement of the finger.

Furthermore, because the camera units 21 are respectively mounted on a plurality of fingertips, for example, a three-dimensional image is able to be generated by use of images captured by the plurality of camera units 21.

Furthermore, because the position sensor 44 that is mounted on the wrist and detects a direction of the arm is included and the camera direction detection unit 46 detects a direction of the camera unit 21, the direction being relative to a reference direction that is the detected direction of the arm, the direction of the camera unit is able to be detected easily by following the direction of the arm moved by the user.

Furthermore, because the myoelectric sensor 22 that detects myoelectric information is mounted on the base portion of the finger on which the camera unit 21 is mounted, or on the wrist, myoelectric information associated with movement of the finger is able to be detected accurately and the direction of the camera unit 21 is able to be detected accurately, the direction being associated with the movement of the finger.

Furthermore, the fingertip camera system 10 includes the fingertip camera device 20 and the three-dimensional image generation processing unit 33 that generates three-dimensional image information representing a three-dimensional structure, on the basis of a plurality of captured images captured by the camera units 21 and directional information indicating relative directions of the camera units 21, the relative directions corresponding to these pieces of imaging information, and thus enables a three-dimensional image to be generated easily.

Embodiments have been described above, but the components of these embodiments do not limit the embodiments. Furthermore, the components described above include those easily predicted by persons skilled in the art, those that are substantially the same, and those of so-called equivalent scope. Furthermore, the above-described components may be combined as appropriate. Furthermore, without departing from the gist of the embodiments described above, various omissions, substitutions, or modifications of the components may be made. For example, in the above-described embodiments, the myoelectric sensor 22 is configured to be provided at the base of a finger, but for example, the myoelectric sensor 22 may be provided integrally with or separately from the control unit 23 mounted on the wrist.

An embodiment enables easy detection of directions of cameras mounted on fingers because a direction of a camera unit relative to a predetermined reference direction is detected based on biological information that has been obtained.

A camera device and a camera system of an embodiment are able to be used, for example, for a fingertip camera device that is mounted on a fingertip and captures an image.

Although the present disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A camera device, comprising:
    a camera unit configured to be mounted on a finger;
    a myoelectric sensor configured to be mounted either on a base of the finger where the camera unit is mounted on a wrist, and configured to detect myoelectric information associated with movement of the finger where the camera unit is mounted, a biological information obtainment unit configured to obtain the myoelectric information transmitted from the myoelectric sensor;
    a camera direction detection unit configured to detect, based on the myoelectric information obtained, camera directional information indicating a direction of the camera unit relative to a predetermined reference direction; and
    an output unit configured to add the camera directional information obtained from the camera direction detection unit to imaging information captured by the camera unit, and output the resulting information.

2. The camera device according to claim 1, wherein
    the camera unit is configured to be mounted on a fingertip of a finger,
    the myoelectric sensor is configured to be mounted on the base of the respective finger, and
    the myoelectric information is associated with movement of a muscle of the finger,
    the camera device further comprising:
    a storage unit configured to store data defining a relation between myoelectric information on a muscle at the base of the finger and directional information on movement of the finger, wherein
    the camera direction detection unit is configured to obtain the directional
    information associated with the detected myoelectric information from the storage unit and detect, from the directional information obtained, the camera directional information.

3. The camera device according to claim 1, further comprising:
    an arm direction detection unit configured to be mounted on a wrist to detect a direction of an arm having the respective finger, wherein
    the camera direction detection unit is configured to detect the camera directional information relative to the reference direction that is the detected direction of the arm.

4. A camera system, comprising:
    the camera device according to claim 1; and
    a three-dimensional image generation processing unit configured to generate, based on a plurality of captured images captured by the camera unit and the camera directional information corresponding to such imaging information thus captured, three-dimensional image information representing a three-dimensional structure.

\* \* \* \* \*